US008506907B2

(12) United States Patent
Angelescu

(10) Patent No.: US 8,506,907 B2
(45) Date of Patent: Aug. 13, 2013

(54) PASSIVE MICRO-VESSEL AND SENSOR

(76) Inventor: Dan Angelescu, Paris (FR)

(*) Notice: Subject to any disclaimer, the term of this patent is extended or adjusted under 35 U.S.C. 154(b) by 175 days.

(21) Appl. No.: 13/025,467

(22) Filed: Feb. 11, 2011

(65) Prior Publication Data
US 2011/0198221 A1 Aug. 18, 2011

Related U.S. Application Data

(60) Provisional application No. 61/337,998, filed on Feb. 12, 2010.

(51) Int. Cl.
F16K 31/12 (2006.01)

(52) U.S. Cl.
USPC .......... 422/550; 422/503; 204/228.4

(58) Field of Classification Search
USPC ........... 204/228.1–230.8; 422/501–512, 422/521, 522, 547, 550–555, 568–570; 251/73, 251/76, 149.8
See application file for complete search history.

(56) References Cited

U.S. PATENT DOCUMENTS

| 1,909,205 | A | 5/1933 | McCollum | 367/58 |
| 3,399,727 | A | 9/1968 | Graham et al. | 166/42 |
| 4,057,780 | A | 11/1977 | Shuck | 340/15.5 MC |
| 4,547,468 | A | 10/1985 | Jones et al. | 501/33 |
| 4,791,251 | A | 12/1988 | Carter et al. | 200/33 R |
| 4,893,505 | A | 1/1990 | Marsden et al. | 73/155 |
| 5,441,110 | A | 8/1995 | Scott, III | 166/308 |
| 5,503,225 | A | 4/1996 | Withers | 166/250.1 |
| 6,443,228 | B1 | 9/2002 | Aronstam et al. | 166/250.11 |
| 6,619,311 | B2 | 9/2003 | O'Connor et al. | 137/109 |
| 6,891,477 | B2 | 5/2005 | Aronstam | 340/606 |
| 6,898,529 | B2 | 5/2005 | Gao et al. | 702/11 |
| 7,082,993 | B2 | 8/2006 | Ayoub et al. | 166/250.1 |
| 7,134,492 | B2 | 11/2006 | Willberg et al. | 166/250.1 |
| 7,216,533 | B2 | 5/2007 | McGregor et al. | 73/152.27 |
| 7,318,912 | B2 | 1/2008 | Pezzuto et al. | 422/103 |
| 7,455,667 | B2 | 11/2008 | Uhland et al. | 604/890.1 |
| 7,712,527 | B2 | 5/2010 | Roddy | 166/250.14 |
| 8,129,318 | B2 | 3/2012 | McDaniel et al. | 507/271 |
| 2007/0048192 | A1 | 3/2007 | Kartalov et al. | 422/100 |
| 2008/0047836 | A1 | 2/2008 | Strand et al. | 204/644 |

(Continued)

FOREIGN PATENT DOCUMENTS

| EP | 0620893 | 12/2000 |
| EP | 1137862 | 3/2004 |

(Continued)

OTHER PUBLICATIONS

Grayson, A.C.R., et al., "Multi-phase drug delivery from a resorbable polymeric microchip device", Nature Materials, vol. 2, Nov. 2003, p. 767-772 + supplemental information.*

(Continued)

Primary Examiner — J. Christopher Ball
(74) Attorney, Agent, or Firm — Sunstein Kann Murphy & Timbers LLP

(57) ABSTRACT

An electrically passive device and method for in-situ acoustic emission, and/or releasing, sampling and/or measuring of a fluid or various material(s) is provided. The device may provide a robust timing mechanism to release, sample and/or perform measurements on a predefined schedule, and, in various embodiments, emits an acoustic signal sequence(s) that may be used for triangulation of the device position within, for example, a hydrocarbon reservoir or a living body.

49 Claims, 8 Drawing Sheets

(56) References Cited

U.S. PATENT DOCUMENTS

| | | | |
|---|---|---|---|
| 2009/0126996 A1 | 5/2009 | Villareal et al. | 175/50 |
| 2009/0288820 A1 | 11/2009 | Barron et al. | 166/249 |
| 2010/0051266 A1 | 3/2010 | Roddy et al. | 166/250.1 |
| 2011/0186290 A1 | 8/2011 | Roddy et al. | 166/253.1 |
| 2012/0037368 A1 | 2/2012 | Eick et al. | 166/300 |
| 2012/0048538 A1 | 3/2012 | Brannon | 166/250.01 |

FOREIGN PATENT DOCUMENTS

| | | |
|---|---|---|
| GB | 2443900 | 5/2008 |
| GB | 2459793 | 11/2009 |
| WO | WO 2011/100509 | 8/2011 |

OTHER PUBLICATIONS

Kwang et al., "Topical review: A review of microvalves", J. Micromech. and Microeng., vol. 16, pp. R13-R39, 2006.

Prescott et al., "Chronic, programmed polypeptide delivery from an implanted, multireservoir microchip device", Nat. Biotech., vol. 24, No. 4, pp. 437-438, Apr. 2006.

Santini, Jr. et al., "Microchips as Controlled Drug-Delivery Devices", Angew. Chem. Int. Ed., vol. 39, pp. 2396-2407, 2000.

Staples et al., "Application of Micro- and Nano-Electromechanical Devices to Drug Delivery", Pharm. Res., vol. 23, No. 5, May 2006.

Stone et al., "Engineering Flows in Small Devices: Microfluidics Toward a Lab-on-a-Chip", Annu. Rev. Fluid Mech., vol. 36, pp. 381-411, 2004.

Vogel et al., "Optical and acoustic investigations of the dynamics of laser-produced cavitation bubbles near a solid boundary", J. Fluid Mech., vol. 206, pp. 299-338, 1989.

International Searching Authority, International Search Report—International Application No. PCT/US2011/024467, dated Sep. 23, 2011, together with the Written Opinion of the International Searching Authority, 8 pages.

Montgomery et al., "Hydraulic Fracturing—History of an Enduring Technology", Jour. of Petrol. Tech., pp. 26-41, Dec. 2010.

Miller et al., "Fracturing Oil Shale with Explosives for in Situ Recovery", Am. Chem. Soc. 167$^{th}$ Nat'l Mtg, Los Angeles—Symposium on Shale Oil, Tar Sands and Related Fuel Sources, Mar. 31-Apr. 5, 1974, pp. 60-85.

Angelescu, "Highly Integrated Microfluidics Design", Artech House, Inc., Norwood MA, 2011.

Beeby et al., "MEMS Mechanical Sensors", Artech House, Inc., Norwood, MA, 2004.

\* cited by examiner

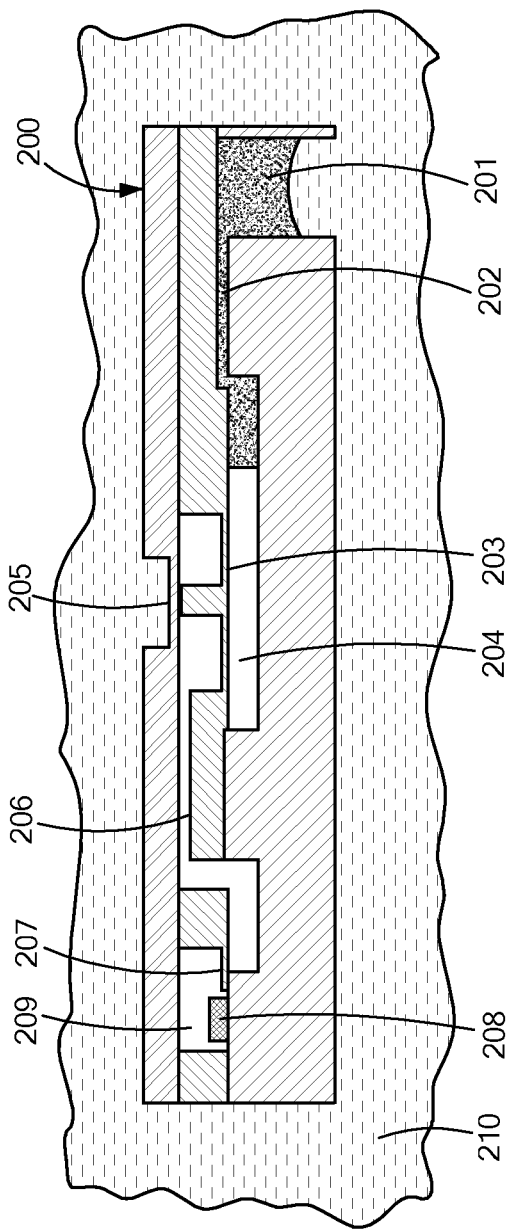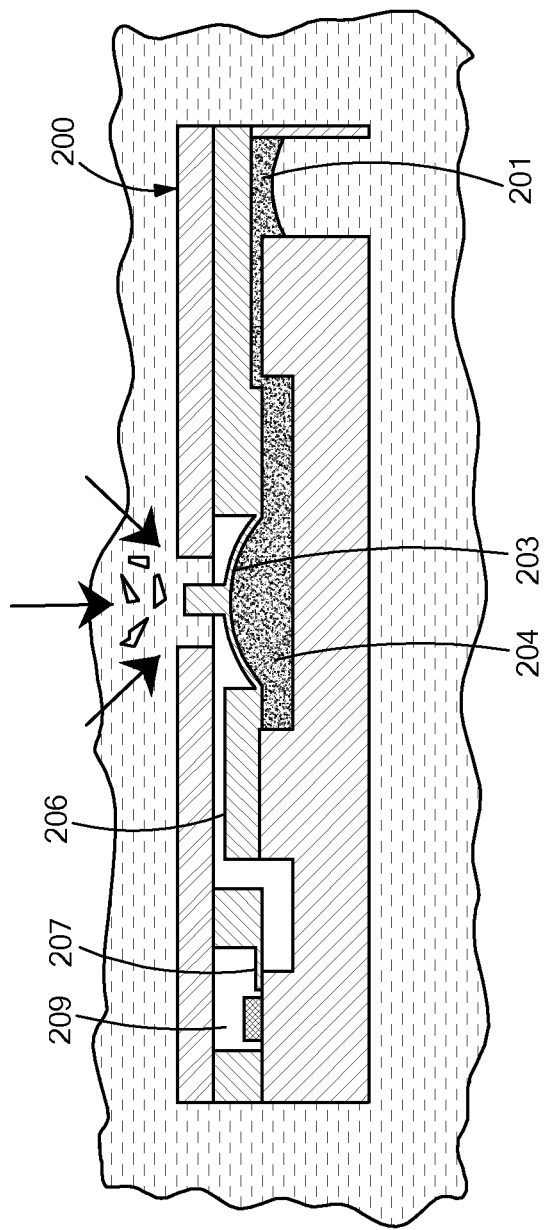

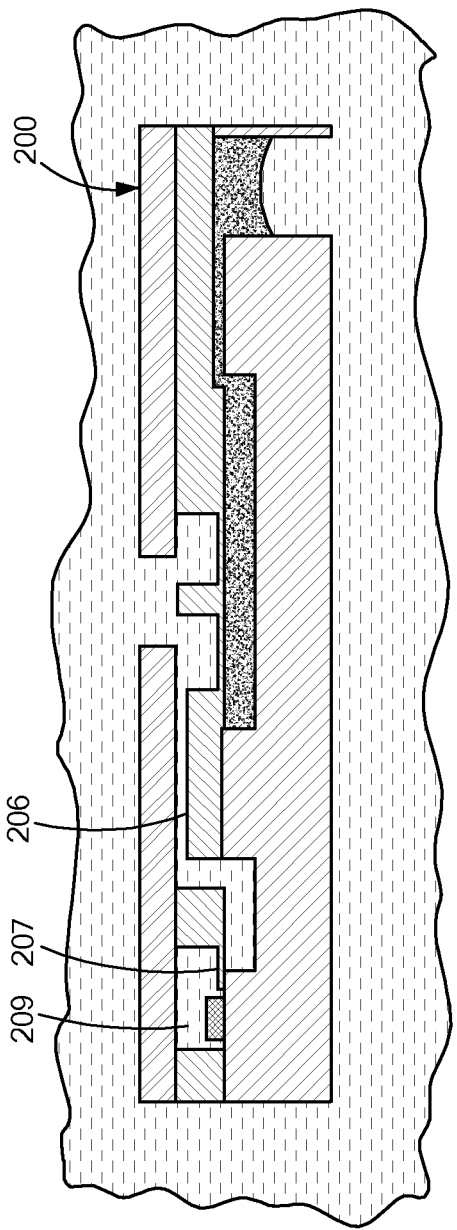
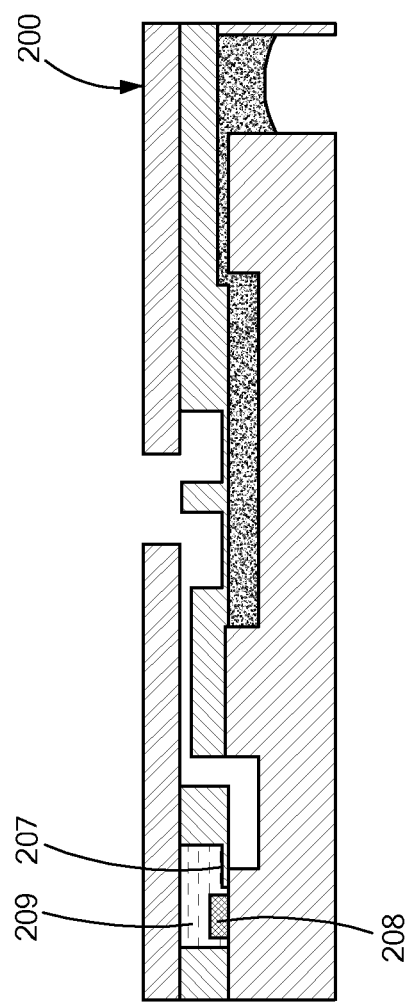
FIG. 2(c)
FIG. 2(d)

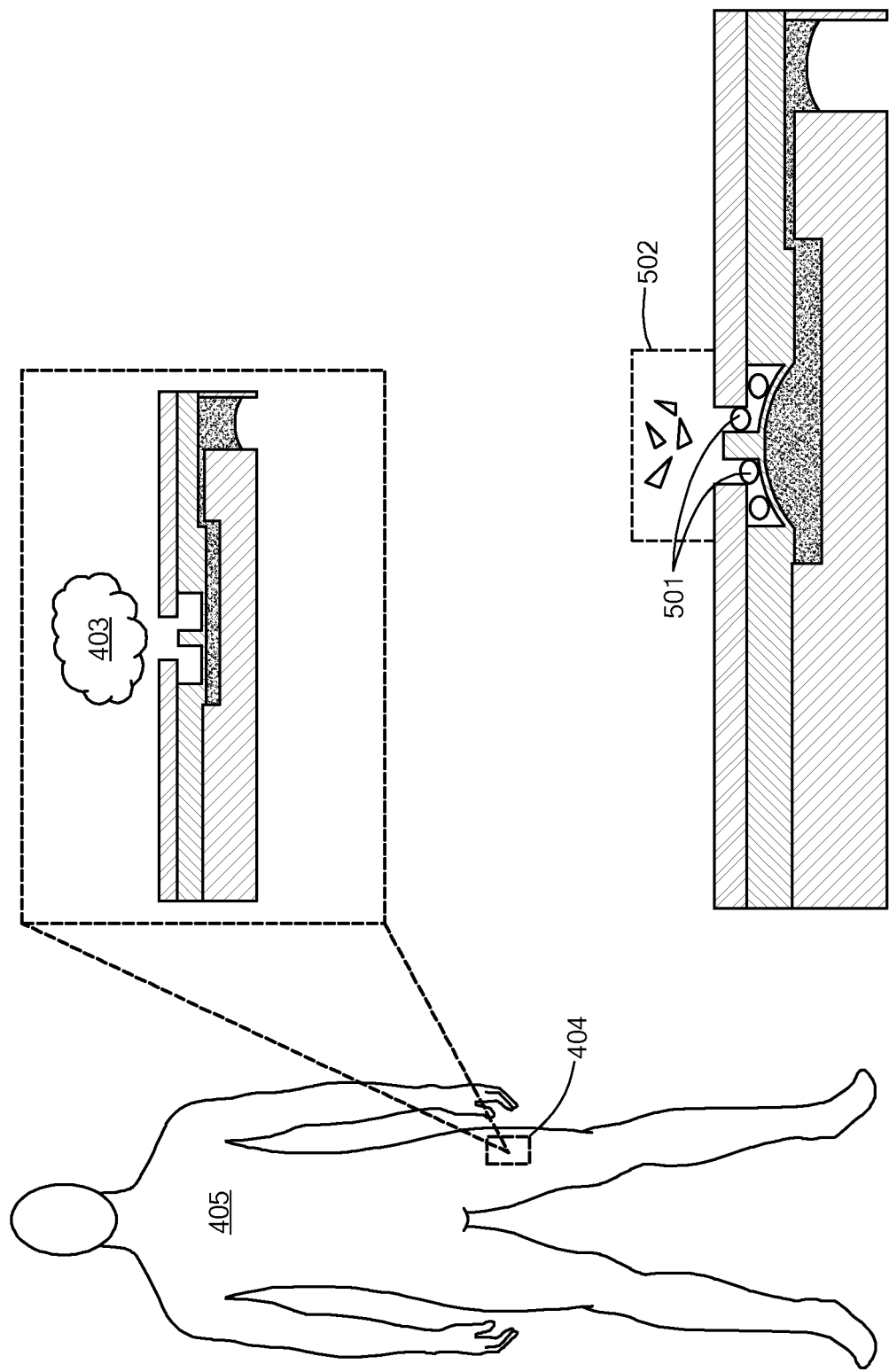

PASSIVE MICRO-VESSEL AND SENSOR

CROSS-REFERENCE TO RELATED APPLICATIONS

This application claims priority from U.S. provisional patent application Ser. No. 61/337,998 filed Feb. 12, 2010, entitled "Passive Micro-vessel and Sensor," which is hereby incorporated herein by reference, in its entirety.

TECHNICAL FIELD

The present invention generally relates to an electrically passive device capable of communicating its position by acoustic emission at specific time intervals, and/or of retrieving and/or sensing fluid samples at specific time intervals, and/or of time-release of particles, chemical products, or pharmaceutical products. More particular embodiments of the present invention relate to an electrically passive vessel for acquiring samples or releasing various particle/products in a subsurface formation (such as a geological or marine formation) or a living body, with the optional capability of providing measurements on the sample, and/or communicating its position via acoustic emissions.

BACKGROUND ART

Obtaining and analyzing samples of fluid from subsurface reservoir formations is often conducted during oil and gas exploration. Such operations are hindered by the harsh subterranean environment specific to oilfields, including high temperature and pressure (HPHT), corrosive fluids, and severely constrained geometry. The difficulty in acquiring and performing measurements on fluidic samples in such an environment are further complicated by use of electronic sensors that typically require power, monitoring and/or telemetry.

Several oil-field related operations, such as fracturing a geological formation, would greatly benefit from the capability of producing a map of the subterranean fracture geometry, and of the fracture evolution in time. Such capability does not currently exist. A similar need exists for a technology which can be used in monitoring and performing fracture analysis of subterranean carbon dioxide sequestration reservoirs.

Measurements of fluid properties and composition far from an oil well are difficult to perform in the oilfield environment. The capability to inject very small sensing devices far into a geological formation by use of a Proppant or similar means of sensor transport, and to be able to determine their position and the precise moment when they perform a measurement or acquire a sample would greatly benefit the industry.

Measurements need to be performed in other types of high-pressure situations, where the deployment of active sensing systems with on-board electronics and data transmission capabilities may either be impossible due to environmental issues (for example temperatures and pressures that are too high) or may prove to be too expensive to justify economically. Typical examples involve measurements within aquifers, portable water wells, or in a submarine environment. Such an environment may be a lake, or a sea or ocean.

Often there is a need for injecting, or liberating, small particles or small amounts of chemicals at predefined times into a remote environment, or into an environment which is difficult to access. Such small particles or chemicals may be used as tracers, may participate in chemical reactions, or may be used as pharmaceuticals. Exemplary environments where such particles, chemicals, or pharmaceuticals may be injected include without limitation oil and water reservoirs, pre-existing or induced fractures within such reservoirs or within other geological formations, oil, water and/or gas wells, water bodies such as lakes, rivers and oceans, or a human body.

Monitoring of hazardous waste disposal reservoirs and of adjacent aquifers for contamination mapping and leaching is also a very important domain, where the need for miniaturized and economical sensing solutions is prominent.

SUMMARY OF THE INVENTION

In accordance with an embodiment of the invention, a device includes at least one sampling mechanism. Each sampling mechanism includes a timing diaphragm, a timing cavity, a mechanical structure and an isolated cavity. Each sampling mechanism further includes a microfluidic channel of predefined geometry filled with a timing fluid having known timing fluid properties. Upon applying pressure to the timing fluid, the timing fluid advances within the microfluidic channel at a speed dictated by the predefined channel geometry and known timing fluid properties. Upon reaching the timing cavity after a timing interval, the timing fluid applies pressure to the timing diaphragm which ruptures and/or collapses the mechanical structure, thus allowing the external fluid to enter the isolated cavity, which may then further lead to a sampling chamber.

In accordance with related embodiments of the invention, the device may include a plurality of sampling mechanisms. At least one sampling mechanism may have a microfluidic channel having different dimensions than another sampling mechanism, such that the timing fluid of the different sampling mechanisms reach their associated cavities at different times. The sampling mechanism may include a check valve that allows flow of fluid into the sampling chamber but prevents flow of fluid out of the sampling chamber.

In accordance with further related embodiments of the invention, an acoustic signal may be emitted from the device upon the mechanical structure rupturing and/or collapsing. The isolated cavity and the mechanical structure may be shaped to emit a predetermined acoustic signal upon the mechanical structure collapsing. The device may include a plurality of sampling mechanisms, each sampling mechanism having an acoustic signature upon collapse of its associated mechanical structure, wherein the acoustic signatures of the sampling mechanisms vary. The device may include a plurality of sampling mechanisms, wherein at least one sampling mechanism has a microfluidic channel having different dimensions than another sampling mechanism, such that the timing fluid of the different sampling mechanisms reach their associated cavities at different times so as to produce multiple acoustic events that occur at different times. The sampling chamber may include a sensor element for performing a detection and/or a measurement on the fluid. The sensor element may include, for example, a material that interacts with the fluid and/or electrodes allowing an electrochemical measurement to be performed on the fluid sample. The device may be electrically passive. The isolated cavity may include a micro-particle, a nano-particle, a chemical product, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with still further related embodiments, a tool may incorporate the above-described device. The tool may have an interior flow-line through which a sample fluid is capable of circulating and in which the one or more devices are positioned, wherein said sample fluid when circulating in the interior flow-line contacts the devices. The tool may include a pad capable of being pushed into a formation wall to receive fluid, and a pump for pumping formation fluid into the interior flow-line. The tool may further include at least one microphone for receiving acoustic emissions from the one or more devices. Other microphones may be located at different positions on the ground in the area surrounding a well, or within wells drilled elsewhere in the formation. The tool may include a processor for performing a time-stamping of the received acoustic emissions and/or a determination of device positioning. The tool may include a retrieval mechanism for retrieving the devices from an underground formation. The retrieval mechanism may include one of a pumping device and a suction device.

In accordance with still further related embodiments, the above-described device may be injected from the surface into an underground formation by pumping it along with a carrier fluid or proppant through a well. Monitoring of the acoustic emissions from the device may be performed using microphones placed in the injection well, in a well drilled elsewhere in the area, or on the ground. The device may be deployed in a pipe, a well, an engine, a hydrocarbon reservoir, an aquifer, a body of water, an oil field tool, a waste disposal reservoir, a proppant formulation and/or a living body.

In accordance with another embodiment of the invention, a device for sampling a fluid includes at least one sampling mechanism, which may be electrically passive. Each sampling mechanism includes an isolated cavity, a mechanical structure and a microfluidic timing mechanism. Upon the microfluidic timing mechanism being subject to pressure, the mechanical structure collapses and/or ruptures after a time delay, allowing external fluid to enter the isolated cavity, which may then further lead to a sampling chamber.

In accordance with related embodiments of the invention, the micro fluidic timing mechanism may include a microfluidic channel filled with a timing fluid, and wherein upon applying pressure to the timing fluid, the timing fluid advances within the microfluidic channel. The timing fluid may advance within the microfluidic channel at a predefined speed dictated, at least in part, by the microfluidic channel geometry and timing fluid properties. The microfluidic timing mechanism may include a timing cavity and a timing diaphragm, and wherein upon the timing fluid advancing and reaching the timing cavity, the timing fluid applies pressure to expand the timing diaphragm, collapsing the mechanical structure and thus allowing the external fluid to enter the isolated cavity. The device may emit a predetermined acoustic signal upon collapse of the mechanical structure. The sample cavity may include a sensor element for performing a detection and/or a measurement on the fluid that enters the sample chamber. The isolated cavity may include a microparticle, a nano-particle, a chemical products, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolated cavity and the environment surrounding the device.

In accordance with further related embodiments of the invention, a system includes one or more of the above-described devices. The system further includes at least one microphone, geophone, accelerometer and/or other type of sensor for receiving acoustic emissions from the one or more devices. A processor may timestamp the received acoustic emissions and/or determine a position of the one or more devices based, at least in part, on the received acoustic emissions. The device may be deployed within a pipe, a well, an engine, a hydrocarbon reservoir, an aquifer, a body of water, an oil field tool, a waste disposal reservoir, a proppant formulation and/or a living body.

In accordance with another embodiment of the invention, a system for sampling a fluid includes at least one device, which may be electrically passive. Each device includes a mechanical structure, and a microfluidic timing mechanism that, upon the microfluidic timing mechanism being subjected to pressure, collapses the mechanical structure after a time delay. Upon collapse the mechanical structure emits an acoustic signature, and may allow fluid to enter a sample chamber. The system further includes a microphone for receiving the acoustic signature, and a processor operatively coupled to the microphone. The processor may, for example, extract the position of the device based, at least in part, on the received acoustic signature.

In accordance with another embodiment of the invention, a method includes deploying a device in a fluid. An acoustic cavity within the device is opened to the fluid, at a time determined by an electrically passive timing mechanism. The device emits an acoustic signature when the cavity is opened.

In accordance with related embodiments of the invention, a sample may be acquired upon opening of the cavity. The acoustic signature may be detected using, at least in part, one or more microphones, geophone, accelerometer and/or other type of sensor. The detected acoustic signature may be time-stamped. The position of the device may be extracted from the detected acoustic signature using, without limitation, triangulation, compressional signal processing, and/or shear signal processing. The device may be deployed in a geological formation or a formation fracture. For example, the device may be pumped into the geological formation. Deploying the device may include using the device in a hydraulic fracturing operation. The device may be deployed in a fluid within a pipe, a fluid within a well, a fluid within an engine, a hydrocarbon reservoir, an aquifer, a body of water, a fluid within an oil field tool, a waste disposal reservoir, a proppant formulation and/or a living body.

In accordance with further related embodiments of the invention, the timing mechanism may include a timing diaphragm, a timing cavity, and a microfluidic channel of known geometry filled with a timing fluid having known timing fluid properties. Upon applying pressure to the timing fluid, said timing fluid advances within the microfluidic channel at a speed dictated by the known channel geometry and known timing fluid properties, and upon reaching the timing cavity after a timing interval, the timing fluid applies pressure to the timing diaphragm which opens the acoustic cavity within the device to the external fluid.

In accordance with still further embodiments of the invention, at least one of a micro-particle, a nano-particle, a chemical products, and a pharmaceutical product may be stored within the device into the external fluid upon collapse of the acoustic cavity. A sample of the external fluid may be stored within the device upon collapse of the acoustic cavity.

In accordance with another embodiment of the invention, a device includes an isolated cavity that is initially inaccessible to an exterior environment, and an electrically passive timing mechanism. A mechanical structure separates the isolated cavity from the exterior environment, such that at the end of a timing interval the timing mechanism acts on the mechanical structure in a way that ruptures and/or collapses it, thus bringing the isolated cavity in contact with the exterior environment.

In accordance with a related embodiment of the invention, the device timing mechanism may include a timing membrane, a timing cavity, and a microfluidic channel of predefined geometry filled with a timing fluid having known timing fluid properties. Upon applying pressure to the timing fluid, the timing fluid advances within the microfluidic channel at a speed dictated by the predefined channel geometry and known timing fluid properties. Upon reaching the timing cavity after a timing interval the timing fluid applies pressure to the timing diaphragm which collapses the mechanical structure, thus allowing external fluid to enter the isolated cavity.

In accordance with further related embodiments of the invention, the device may include an external device for applying pressure to the timing fluid. The mechanical structure may be an isolation membrane and/or diaphragm. The isolated cavity may include a sampling chamber, the sampling chamber including a check valve that allows flow of fluid into the sampling chamber but prevents flow of fluid out of the sampling chamber. An acoustic signal may be emitted from the device upon rupture of the mechanical structure. The isolated cavity and the mechanical structure may be shaped to emit a predetermined acoustic signal upon the mechanical structure collapsing. The isolated cavity may include a sensor element for performing a detection and/or a measurement on the fluid. The sensor element may include a material that interacts, such as chemically, with the fluid. The sensor element may include an electrode, allowing, for example, an electrochemical measurement to be performed on the fluid sample. The sensor element may be a Micro-Electro-Mechanical Systems (MEMS) device that may be microfabricated.

In accordance with yet further embodiments of the invention, the isolated cavity may include a micro-particle, a nano-particle, a chemical products, and/or a pharmaceutical product, which is released into the environment after the collapse and/or rupture of the mechanical structure separating the isolated cavity from the exterior environment. The device may include a filter and/or a sieve to retain broken mechanical structure parts from entering at least one of the isolation cavity and the environment surrounding the device.

In accordance with additional related embodiments of the invention, the device may include a plurality of isolated cavities, a plurality of passive timing mechanisms, and a plurality of mechanical structures. At least one of the passive timing mechanisms may have a timing interval different from the other timing mechanisms, such that the mechanical structures associated with the at least one passive timing mechanism ruptures and/or collapses at a different time.

In accordance with still further related embodiments of the invention, a system may include a plurality of the above-described devices, wherein each device has an acoustic signature upon collapse of its associated mechanical structure, wherein the acoustic signatures of the devices vary. A system may include a plurality of the above-described devices, wherein at least one device has a microfluidic channel having different dimensions than another device in the system, such that the timing fluid of the different sampling mechanisms reach their associated cavities at different times so as to produce multiple acoustic events that occur at different times. A tool may incorporate one or more of the above-described devices, the tool having an interior flow-line through which a sample fluid is capable of circulating and in which the one or more devices are positioned, wherein said sample fluid when circulating in the interior flow-line contacts the devices. The tool may further include at least one microphone for receiving acoustic emissions from the one or more devices, and a processor for performing timestamping of the received acoustic emissions and/or determination of device positioning. A method using at least one of the above-described devices may include deploying the device within one of a pipe, a well, an engine, a hydrocarbon reservoir, an aquifer, a body of water, a waste disposal reservoir, an oil field tool, a proppant formulation and a living body.

In accordance with yet further related embodiments of the invention, a system may include a plurality of the above-described devices, wherein the system is incorporated into an underwater measurement system. The system may be attached or otherwise embedded in a cable. The cable may be further attached to a fixed buoy, or towed through a body of water by a ship or an underwater vehicle.

In accordance with another embodiment of the invention, a method includes deploying a device in an external fluid. A cavity is opened within the device to the external fluid, at a time determined by an electrically passive timing mechanism. Upon the cavity opening, a micro-particle, a nano-particle, a chemical products, and/or a pharmaceutical product is released from the cavity into the external fluid, and/or a sample of the external fluid may be stored within the device.

In accordance with related embodiments of the invention, the passive timing mechanism may include a timing diaphragm, a timing cavity; and a microfluidic channel of known geometry filled with a timing fluid having known timing fluid properties. Upon applying pressure to the timing fluid, said timing fluid advances within the microfluidic channel at a speed dictated by the known channel geometry and known timing fluid properties, and upon reaching the timing cavity after a timing interval, the timing fluid applies pressure to the timing diaphragm which opens the cavity within the device to the external fluid.

In accordance with further related embodiments of the invention, deploying the device may include pumping the device into a geological formation and/or a formation fracture. The device may be deployed in a pipe, a well, an engine, a hydrocarbon reservoir, an aquifer, a body of water, an oil field tool, a waste disposal reservoir, a proppant formulation and/or a living body.

In accordance with still further embodiments of the invention, the method may include emitting by the device an acoustic signature when the cavity is opened. The acoustic signature may be detected using, at least in part, one or more microphone. A position of the device may be extracted from the detected acoustic signature using triangulation, compressional signal processing, and/or shear signal processing.

In accordance with another embodiment of the invention, a device includes an electrically passive timing mechanism and a mechanical structure. At the end of a timing interval, the timing mechanism ruptures the mechanical structure so as to emit an acoustic signal.

In accordance with related embodiments of the invention, the device may include an isolated cavity, wherein the mechanical structure separates the isolated cavity from the exterior environment, and wherein rupturing the mechanical structure brings the isolated cavity in contact with the exterior environment. The mechanical structure may be an isolation membrane.

In accordance with further embodiments of the invention, the timing mechanism may include a timing diaphragm and a timing cavity. A micro fluidic channel of known geometry is filled with a timing fluid having known timing fluid properties, such that upon applying pressure to the timing fluid, the timing fluid advances within the microfluidic channel at a speed dictated by the known channel geometry and known timing fluid properties. Upon reaching the timing cavity, the timing fluid applies pressure to the timing diaphragm which ruptures and/or collapses the mechanical structure, which thus may allow external fluid to enter the isolated cavity. The isolated cavity may include a sampling chamber, the sampling chamber including a check valve that allows flow of fluid into the sampling chamber but prevents flow of fluid out of the sampling chamber. The sampling chamber may include a sensor element for performing at least one of a detection and a measurement on the fluid. The sensor element may include a material that interacts with the fluid. The sensor element may include electrodes allowing an electrochemical measurement to be performed on the fluid sample.

In accordance with further related embodiments of the invention, the mechanical structure may be shaped to emit a predetermined acoustic signature upon rupturing. The device may be microfabricated.

In accordance with still further related embodiments of the invention, a system includes a plurality of the above-described devices, wherein each device has an acoustic signature upon rupture of its associated mechanical structure, wherein the acoustic signatures of the devices vary. The system may be incorporated into an underwater measurement system. The devices may be attached to a cable. The cable may be towed through a body of water by one of a ship and an underwater vehicle. The device(s) may be used during a hydraulic fracturing operation.

In accordance with various embodiments of the invention, the timing fluid in the above-described embodiments may either be a Newtonian fluid of known viscosity or a non-Newtonian fluid of known rheology. A complex non-Newtonian shear-thinning fluid may have a number of advantages, namely the fact that the non-Newtonian timing fluid will have a very high viscosity at low shear stress (i.e. at low applied pressure), but the viscosity will drop rapidly as the stress is increased. In various embodiments of the invention, a complex non-Newtonian fluid may be used as a timing fluid, resulting in a timing mechanism which only becomes active once the ambient pressure has reached a certain threshold value and providing additional versatility to the timing mechanism.

BRIEF DESCRIPTION OF THE DRAWINGS

The foregoing features of the invention will be more readily understood by reference to the following detailed description, taken with reference to the accompanying drawings.

FIGS. 2(a-d) show the device of FIG. 1 in more detail, in accordance with an embodiment of the invention. FIG. 2(a) shows the device prior to activation. FIG. 2(b) shows the device with the isolation membrane collapsed. FIG. 2(c) shows the device with the sample chamber filled with sample fluid. FIG. 2(d) shows the device ready to be interrogated after surface retrieval.

FIG. 4 shows a passive timing device that includes a pharmaceutical product for release within a human body, in accordance with an embodiment of the invention.

FIG. 5 shows a passive timing device that includes a filter for containing the broken diaphragm particles, in accordance with an embodiment of the invention.

DETAILED DESCRIPTION OF SPECIFIC EMBODIMENTS

In illustrative embodiments, an electrically passive device and method for in-situ acoustic emission, and/or releasing, sampling and/or measuring of a fluid or various material(s) is provided. The device may provide a robust timing mechanism to release, sample and/or perform measurements on a predefined schedule, and, in various embodiments, emits an acoustic signal sequence(s) that may be used for triangulation of the device position within, for example, a hydrocarbon reservoir or a living body. Details are discussed below.

Figure 1:
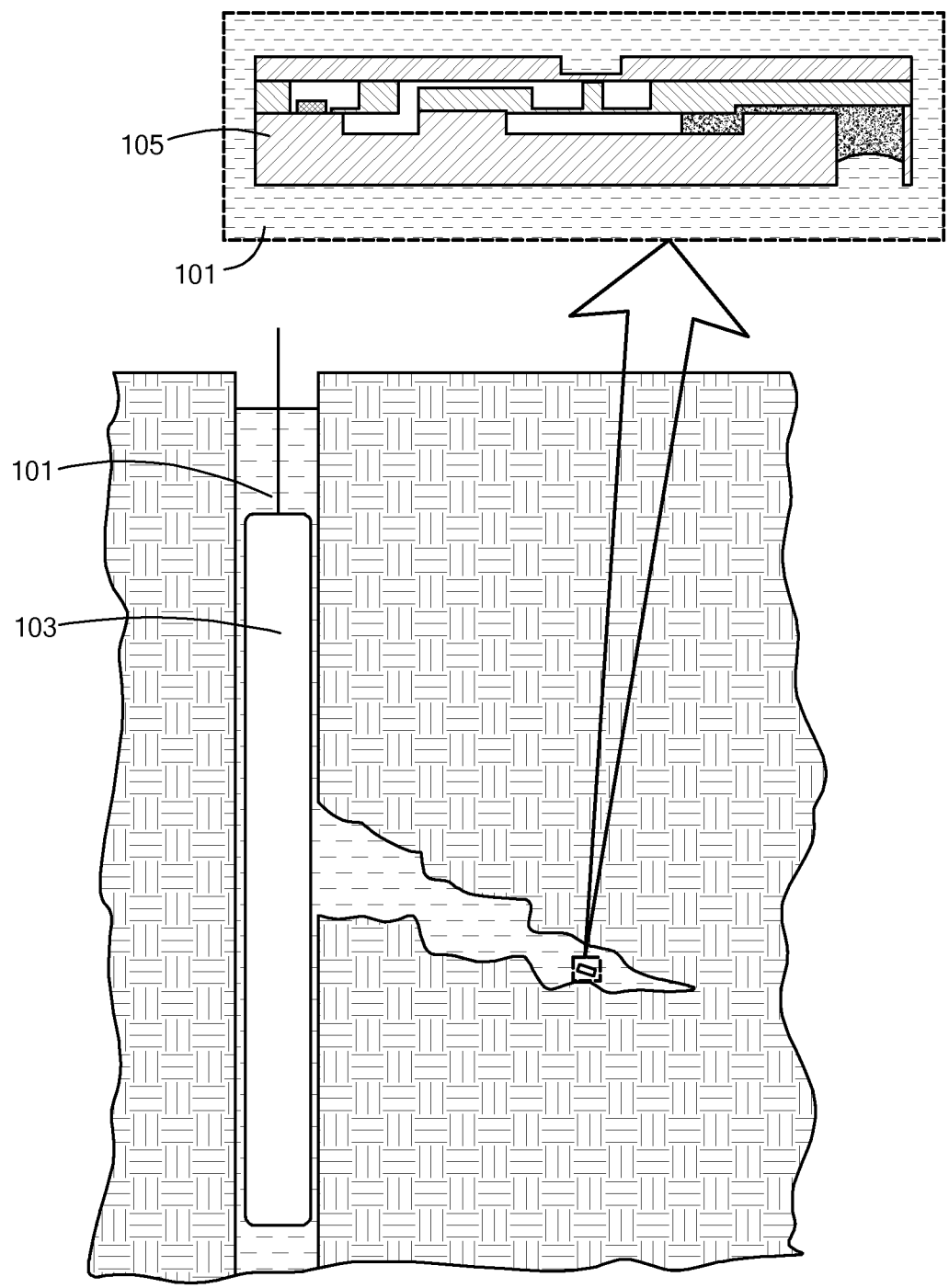
FIG. 1 shows deployment of a device for use in sampling hydrocarbons during fracturing or fluid injection operations, in accordance with an embodiment of the invention.

FIG. 1 shows deployment of a device 105 for use in sampling hydrocarbons during fracturing or fluid injection operations, in accordance with an embodiment of the invention. It should be noted that discussion of the specific device 105 shown, for use in sampling hydrocarbons, is for illustrative purposes only. Other device configurations and applications are within the scope of the present invention. For example, the device 105 may be deployed, without limitation, within a pipe, a well, an engine, a hydrocarbon reservoir, an aquifer, a body of water, an oil field tool, a waste disposal reservoir, a proppant formulation and a living body to release, sample or measure various fluids or other material(s).

The device 105 may be deployed, without limitation, in downhole fluid 101 within a fracture in an underground formation. The device may be, for example, pumped or otherwise injected, into the rock matrix. The device 105 may work in combination with conventional oilfield measurement tools 103 or autonomous battery-operated sensors, that may be placed in the well in hydraulic communication with the fracture where the device 105 is injected. The device 105 may be used at very high pressures or temperatures, thus providing a pathway to performing measurements within wells which are currently inaccessible to existing sensor technology due to, without limitation, severely constrained geometry, corrosive fluids, elevated pressure and/or temperature. Examples of adverse well environments include recently developed deep-sea well reservoirs in the Gulf of Mexico.

FIGS. 2(a-d) show the device in more detail, in accordance with various embodiments of the invention. FIG. 2(a) shows the device 200 prior to activation. The device 200 includes at least one sampling mechanism for obtaining a sample of the external oil-well fluid 210.

In illustrative embodiments, the sampling mechanism includes a microfluidic timing mechanism for obtaining the fluidic sample. More particularly, the microfluidic timing mechanism may include a microfluidic channel 202 partially filled with a timing fluid 201. Capillary trapped timing fluid 201 may initially be held in place within the microfluidic channel by, without limitation, surface tension. The microfluidic channel 202 leads to a timing cavity 204 of known volume. The timing cavity 204 may initially be, without limitation, empty.

Upon applying pressure to the timing fluid 201, the timing fluid 201 advances within the microfluidic channel 202 into the timing cavity 204 such that it causes a mechanical structure 205 to rupture (and/or collapse) after a time delay. Prior to rupturing, the mechanical structure 205 isolates an isolated cavity 206, which may include a sample chamber 209, from the external environment. The mechanical structure 205 may be, without limitation, an isolation diaphragm or isolation membrane that provides a barrier from the external environment. An example of a delayed actuator with a visco-elastic timer is described in U.S. Pat. No. 4,791,251 (Carter et al.), which is hereby incorporated by reference, in its entirety.

Illustratively, the timing fluid 201 entering the timing cavity 204 may cause a timing diaphragm 203 to deflect. A protrusion or other shaped structure on the timing diaphragm 203 may then rupture the mechanical structure 205. Various other membrane rupture mechanisms known in the art of microfluidic systems, such as in systems used to provide drug encapsulation and delivery, may be utilized (see, for example, M. Staples et al.: Pharm. Res., 23,847 (2006); J. T. Santini et al.: Angew. Chem. Int. Ed. 39, 2396 (2000); J. H. Prescott et al.: Nat. Biotech. 24, 437 (2006), U.S. Pat. No. 7,455,667 (B2), each of which is incorporated herein by reference in its entirety).

FIG. 2(b) shows the device 200 with the mechanical structure 205 collapsed after applying pressure to the timing fluid 201 (and after the time delay). The collapse of the mechanical structure 205 allows external downhole fluid to enter a sample chamber 209 via a isolated cavity/communication channel 206. A particle filter may be placed within the isolated cavity/communication channel 206 to filter any contaminants. Note that prior to collapse of the mechanical structure 205, the isolated cavity/communication channel 206 is typically inaccessible to the exterior environment. In other embodiments, the mechanical structure 205 may allow partial/filtered access to the isolated cavity/communication channel 206 prior to its collapse.

FIG. 2(c) shows the device 200 with the sample chamber 209 filled with sample fluid. An integrated one-way valve 207 (i.e., a check valve), may assure sample isolation from the external environment. An example of a micro-fabricated one-way valve is described in the following documents: S. Beeby, G. Ensel, M. Kraft: *MEMS Mechanical Sensors*, Artech House, Boston Mass. (2004); and K. W. Oh et al.: J. Micromech. Microeng., 16, R13-R39 (2006), each of which is incorporated herein by reference in its entirety.

The timing mechanism, the sampling mechanism, and/or in various embodiments, the entire device, may be electrically passive such that it does not include any powered electronic components (e.g., an electronic power source, transmitter, amplifier etc. . . . ). In various embodiments, the timing mechanism, the sampling mechanism, and/or the entire device may be void of any active or passive electronic components.

The passive microfluidic timing mechanism may be based, at least in part, on the fact that the flow rate f of a Newtonian fluid through a capillary of roughly circular cross-section is proportional to the difference in pressure $\Delta P$ between the ends of the capillary multiplied by the fourth power of the hydraulic radius R, and is inversely proportional to the viscosity of the fluid $\eta$ multiplied by the length of the capillary l: $f = \pi \cdot \Delta P \cdot R^4/(8 \cdot \eta \cdot l)$. In other embodiments, if the capillary is chosen to have a rectangular cross-section with width w and height h<w, the flowrate f can be calculated with the approximate formula: $f=(1-0.63 \, h/w) \cdot \Delta P \cdot w \cdot h^3/(12 \cdot \eta \cdot l)$. Such formulae may be found in the literature, for example in the following documents: Stone, H., Stroock, A., and Ajdari, A., "Engineering Flows in Small Devices," Annual Review of Fluid Mechanics, Vol. 36, 2004, p. 381 and D. E. Angelescu: "Highly Integrated Microfluidics Design", Artech House, Norwood Mass. USA (2011), each of which is incorporated herein by reference in its entirety.

If an empty cavity of known volume (i.e., the timing cavity 204) is separated from a high-pressure fluid by a capillary of appropriate geometry, the time required to fill the timing cavity 204 can be accurately determined from knowledge of device geometry, fluid viscosity and pressure differential. Assuming the timing fluid 201 has known characteristics, and that the pressure/temperature history is recorded, the filling time of the timing cavity 204 can be fully determined by geometrical device parameters such as timing cavity 204 volume, micro-fluidic channel 202 capillary diameter and length; the fourth power dependence on diameter allows control of the fill-up time over several decades, resulting in a very versatile timing mechanism. A fully characterized timing fluid 201 may be used that advantageously may be immiscible with both hydrocarbons and water. Examples of such timing fluids include, without limitation, various silicone oils and fluorinated solvents.

Alternatively, a non-Newtonian fluid with known rheological properties can be used as a timing fluid. In one embodiment, one may use a shear-thinning fluid as a timing fluid, which will result in a flowrate which is very low at low pressures, but increases significantly once the ambient pressure (and hence the shear stress in the microchannel) reaches a certain threshold value. In another embodiment, the timing fluid may be a visco-elastic fluid which behaves as an elastic body at low shear stresses, thus completely blocking flow at low pressures. As the pressure reaches a threshold value (corresponding to the yield stress of the timing fluid), the timing fluid will start flowing. This embodiment allows the passive timing devices described above to be inactive below a certain threshold pressure, thus allowing prolonged storage at a pressure situated below the threshold pressure.

FIG. 2(d) shows the device 200 ready to be interrogated after surface retrieval. The sample fluid stored in the sample chamber 209 remains isolated from the environment by the one-way valve 207, so that various physical and chemical property measurements can be obtained. A sensor may be positioned within, or otherwise operationally coupled to, the sample chamber 209 and/or isolated cavity 206, so as to provide various indications or measurements associated with the sample fluid. In various embodiments, a micro-electro-mechanical sensor (MEMS) design may provide hermetic encapsulation of sensor components within, for example, the sample chamber 209. The sensor may include a material that chemically reacts with the fluid, and/or an electrode allowing an electrochemical measurement to be performed on the fluid sample.

The above-described timing mechanism in conjunction with passive actuators may thus be used to deploy self-triggering sample acquisition devices/vessels. For deployment within a rock matrix, such devices may be density-matched to an injection fluid by incorporating vacuum cavities of appropriate dimensions, which will facilitate passive deployment by injection as well as device retrieval.

Acoustic Emission and Triangulation

Figure 3A:
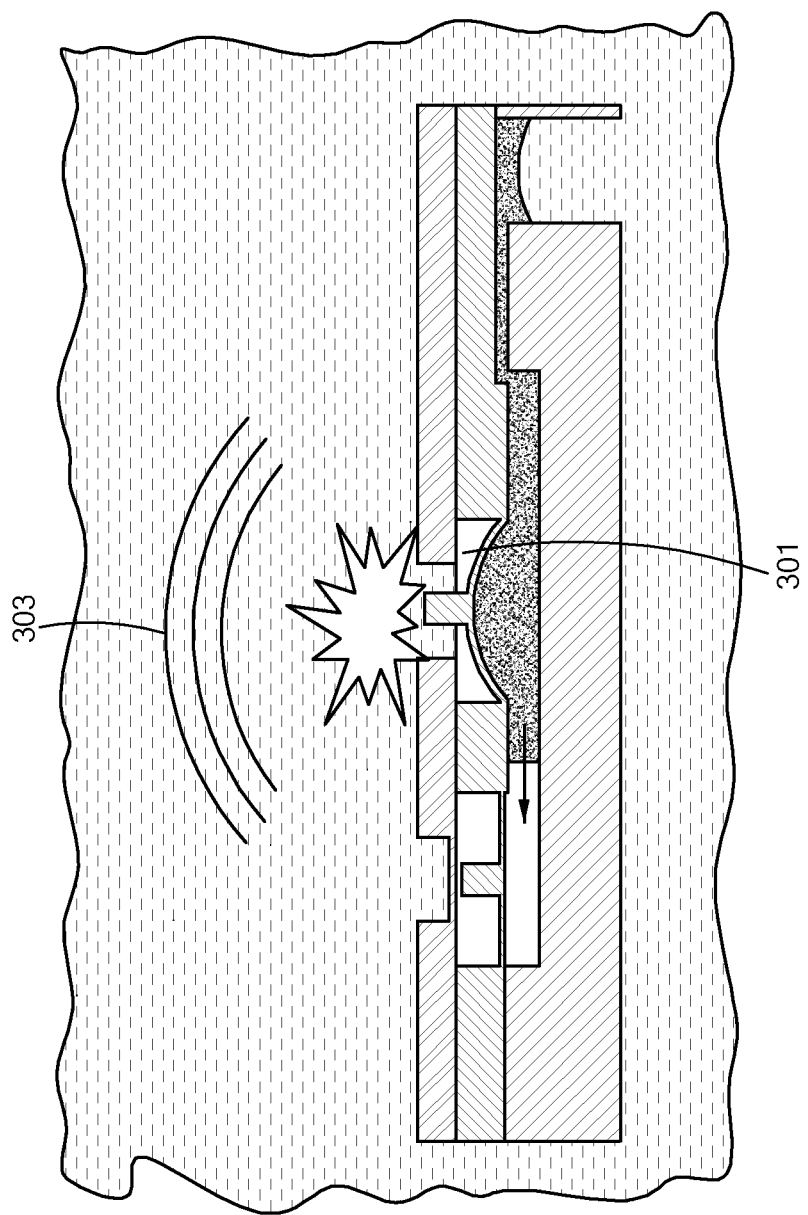
FIG. 3(a) shows a burst of acoustic energy resulting from the rupturing of an isolation membrane, in accordance with an embodiment of the invention.

The above-described device for sample acquisition may be used to generate acoustic signals. For example, in various embodiments the timing mechanism may trigger the piercing of multiple mechanical structures/isolation diaphragms, possibly in sequence. For example, if the cavity behind each isolation diaphragm has volume V (initially under vacuum), upon piercing, these cavities will suddenly collapse and/or rupture, and fill with reservoir fluid at the ambient hydrostatic pressure. The filling of the empty cavity 301 may be very sudden, and will emit a very short burst of acoustic energy 303, as shown in FIG. 3(a), in accordance with an embodiment of the invention. Laboratory studies of collapsing bubbles have been performed by others (for example, A. VOGEL, W. LAUTERBORN, R. TIMM: "Optical and acoustic investigations of the dynamics of laser-produced cavitation bubbles near a solid boundary", J. Fluid Mech., Vol. 206, pp. 299-338 (1989), which is incorporated herein by reference in its entirety), proving that the majority of the bubble energy is emitted into the acoustic transients. The total amount of energy that may be released by sudden filling of a cavity may be roughly estimated as $E=pV$, where p is the reservoir pressure. For an exemplary volume of 1 mm$^3$ and an ambient pressure of 1000 Bar (app. 14500 psi), this corresponds, without limitation, to an emission energy of 100 mJ in a time interval of approximately a fraction of a thousandth of a second to a few thousandths of a second. This corresponds to an acoustic power of over 10-1000 W during each collapse event. Such acoustic emission can then be detected and recorded using remote microphones, hydrophones, geophones, accelerometers or other types of sensors or recorders.

The timing mechanism may trigger several acoustic events in sequence, with the time delay between consecutive collapses defined by the geometry of the associated microfluidic channel and timing cavity. Each device and/or sampling mechanism may be built with a different timing sequence, or with different geometrical parameters, to provide a unique acoustic signature. Such devices may also be realized without a sampling cavity, with the sole purpose of emitting a sound at a time determined by the microfluidic timing mechanism.

Figure 3B:
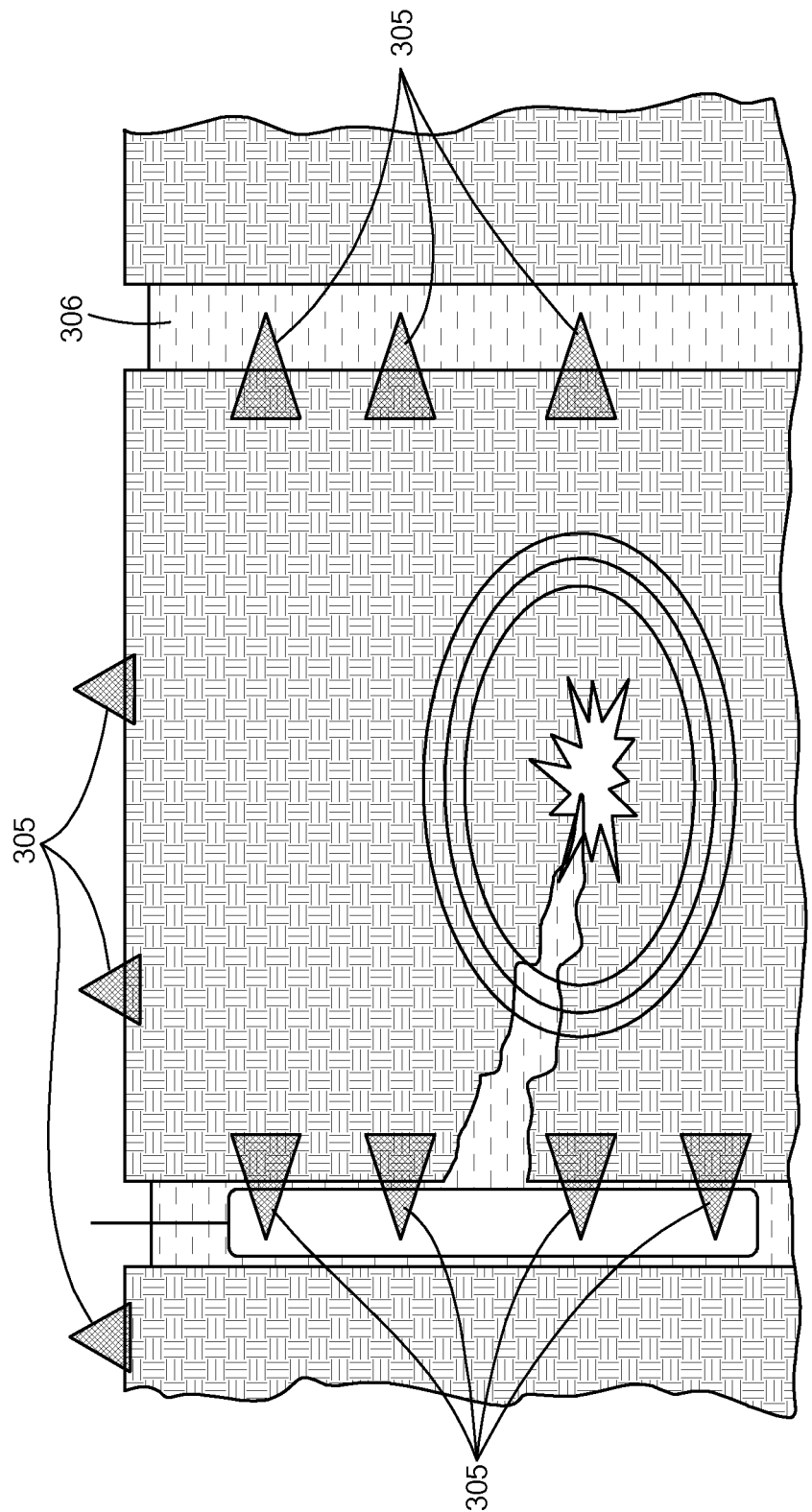
FIG. 3(b) shows multiple microphones placed at different positions in the formation, for recording the arrival time of the wavefronts caused by ruptured isolation membranes, in accordance with an embodiment of the invention.

The acoustic emission for each collapse event will create an acoustic wavefront 303 which will propagate through the fluid and the surrounding rock matrix. The velocity of the wavefront will typically be equal to the sound velocity in the fluid, or in the rock matrix. By placing multiple microphones 305 at different positions in the formation, as shown, for example, in FIG. 3(b), the arrival time of the wavefronts at each microphone 305 may be determined. Based on the time delays between the arrival of the acoustic signal at the different microphones, combined with a knowledge or an educated estimation of the sound velocity in the medium, the position of the smart vessel can then be determined, using, without limitation, triangulation, similar to an underground GPS system, or using compressional/shear signal processing. The time of the sample acquisition may also be recorded. It is noted that FIG. 3(b) is by no way limited to the shown configuration of microphones or devices. In other embodiments of this invention, additional microphones may be located on the ground around the well, or at other subterranean locations, such as in a nearby well 306, cavities, or holes.

Usage as Vehicle for Time-Release of Particles, Chemical Products, or Pharmaceutical Products The above-described devices may be used as vehicles for transport and time-release of, without limitation, micro- and nano-particles, chemical and/or pharmaceutical products, by including the products or particles within the isolated cavity and/or sampling chamber separated by the mechanical structure (e.g., isolation diaphragm). The timing mechanism may trigger the piercing of the isolation diaphragm after a time delay as described above, at which point the fluid surrounding the device penetrates within the cavity behind the isolation diaphragm and comes in contact with the particles, chemical and/or pharmaceutical products. The particles or products may then dissolve within, or mix with the fluid surrounding the device, thus releasing said particles or chemical or pharmaceutical products into the surrounding environment.

Said particles or chemical products or pharmaceutical products may include, without limitation, chemicals for sanitizing water or other fluids; fluorescent chemicals that may be used as flow tracers; various chemical reagents and chemical cleaning agents; pharmaceutical products such as medications or drugs; various types of nutrients; micro- or nano-particles to be used as flow tracers; and/or chemically-functionalized micro- and nano-particles which can react to some environmental parameter.

In accordance with an embodiment of the invention, a passive timing device such as the one previously described may be injected into a geological formation or in a hydraulic fracture by means of pumping via an injection well. When the timing mechanism triggers the piercing of the isolation membrane, functionalized nanoparticles are released within the geological formation as described above. The nanoparticles react with the local environment, are carried by flow towards the injection well, and are retrieved from the well at the surface. The nanoparticle size may be chosen to be substantially smaller than the average pore throat diameter, which will insure that the particle will be transported by flow within the geological formation without clogging the pores. By analyzing the particles after retrieval at the surface, one will be able to infer information about the environment within the geological formation at the time of nanoparticle release. By injecting multiple such passive timing devices which are triggered at different times, one may be able to continuously monitor one or several parameters at multiple remote locations within the geological formation, which may be otherwise inaccessible.

FIG. 4 shows a passive timing device 404 that includes, without limitation, a pharmaceutical product 403 that is released within a human body 405, in accordance with an embodiment of the invention. The isolation diaphragm(s) is pierced at times set by the passive timing device, whereupon the corresponding pharmaceutical products 403 positioned, without limitation, within the isolated cavity and/or sampling chamber, are released within the human body. Multiple devices with one or more diaphragms may be utilized. Using such a system, complete treatment plans may be delivered without any active intervention, by adjusting the timing parameters and the types and quantities of pharmaceutical products within each cavity.

The device 404 may be attached to the skin of the human body 405, or may be implanted within the body. An external source of pressure, or an external pump, may be used to drive the timing fluid within the timing cavity of the device 404. In one embodiment, such external source of pressure may be, without limitation, a pressurized gas cartridge.

FIG. 5 shows a passive timing device that includes a filter 502 for containing the broken diaphragm particles, in accordance with an embodiment of the invention. Upon piercing of the mechanical structure (e.g., isolation diaphragm), the filter 502 advantageously prevents the broken diaphragm particles from passing into the external fluid, while still allowing, for example, a pharmaceutical product 501 to freely pass through. This embodiment may be particularly important if the passive timing device is going to be included within a human body.

Tool Implementation

The above-described devices may also be integrated within downhole sampling and measurements tools, such as the Modular Formation Dynamics Tester (MDT) produced by Schlumberger, the Formation Multi-Tester (FMT) produced by Baker Hughes or the Sequential Formation Tester (SQT) produced by Halliburton, or any other similar tool. Arrays of the sampling devices, integrating a plurality of devices and/or sampling mechanisms on a single microfabricated substrate, may be incorporated within the tool architecture.

Figure 6:
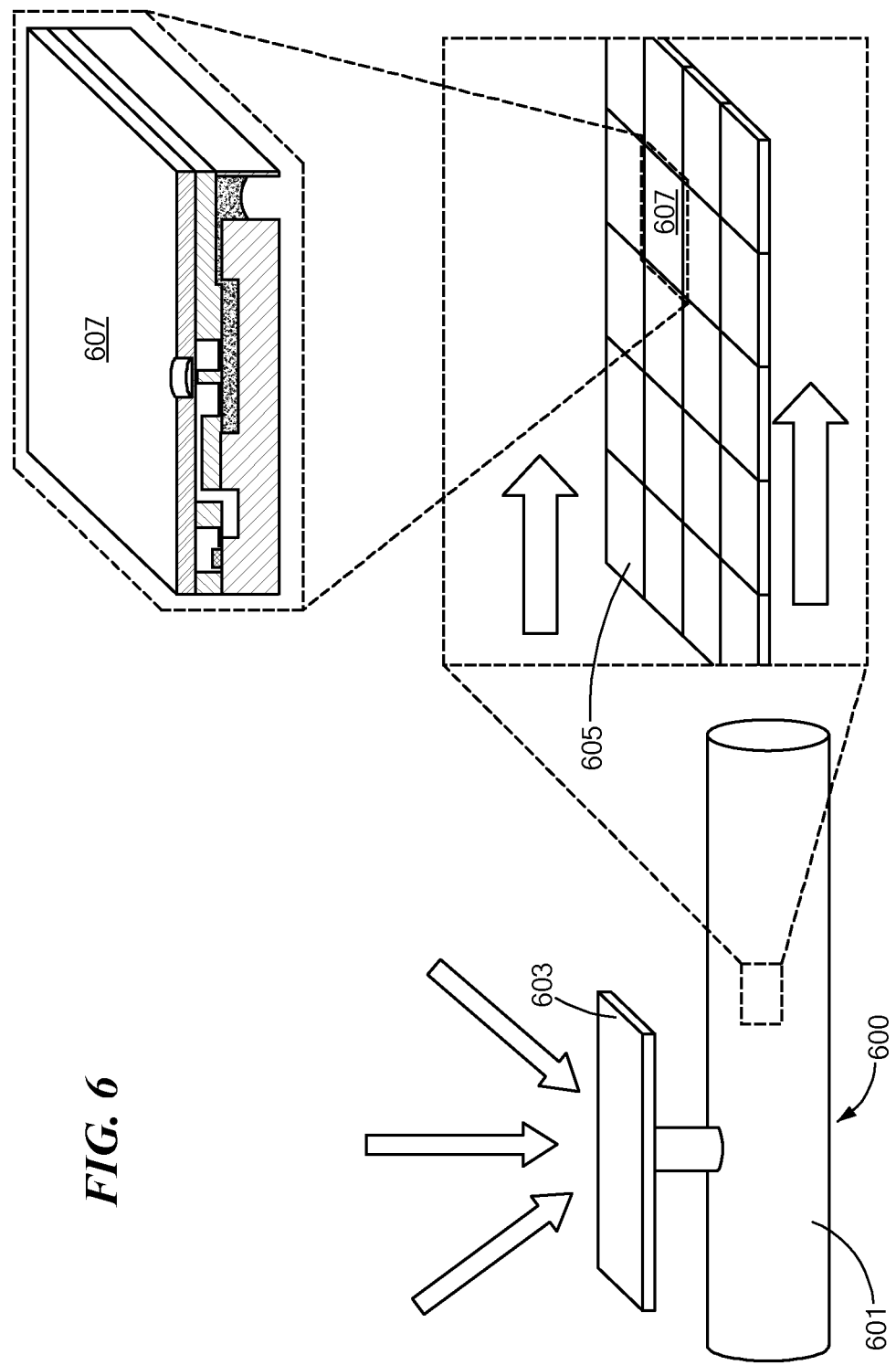
FIG. 6 shows integration of a plurality of sampling devices and/or mechanisms within an oilfield-sampling tool, in accordance with an embodiment of the invention.

FIG. 6 shows integration of a plurality of sampling devices and/or mechanisms 605 within an oilfield-sampling tool such as a MDT, a FMT or a SFT, in accordance with an embodiment of the invention. The tool 600 pushes a pad 603 into the geological formation wall, and pumps the formation fluid into an internal flow-line 601, where the fluid comes into contact with a smart sampling device array 605. Each device 607 may acquire a sample, perform a measurement, and/or emit an acoustic signal which is recorded by a microphone within the tool. The recorded acoustic signals may provide, for example, the precise time when each measurement was performed and may uniquely identify the device which performed the measurement.

The device 607 may come into contact with the formation fluid as it is pumped into the tool flowline 601. The acoustic emission events may be recorded using a microphone implemented in the tool, and later analyzed at the surface to infer the precise time of sample acquisition for each of the smart vessels in the array, thus providing very valuable time-series data.

Figure 7:
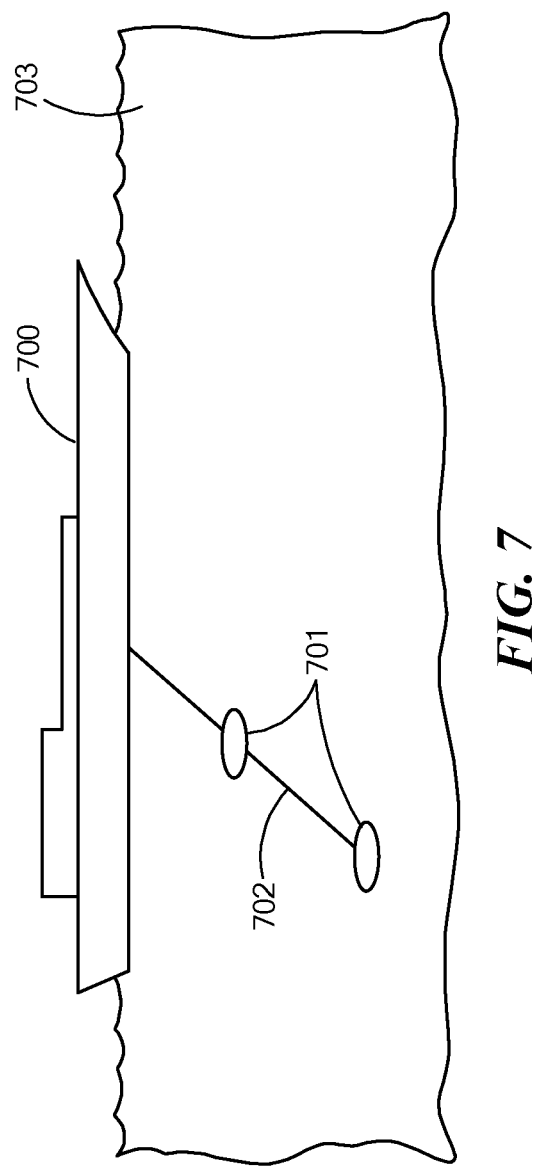
FIG. 7 shows an array of smart sampling devices embedded within an underwater measurement system which may be attached with a cable to either a buoy, a rig, a vessel or a ship, in accordance with an embodiment of the invention.

FIG. 7 shows another embodiment of the invention, where an array of smart sampling devices is embedded within a submarine measurement system 701, which may be attached with a cable 702 to, without limitation, either a buoy, a rig, a submarine, a vessel or a ship 700. The measurement system 701 may either be positioned in a stationary manner in the body of water 703, at a depth dependent, without limitation, on the length of the cable 702, or it may be dragged through the body of water by the ship 700. The smart sampling devices in the measurement system 701 perform sample acquisitions and measurements at times determined by their respective timing mechanisms, thus providing a time-series or a spatial map of measurements at a given depth.

Built-in Redundancy

Due to the impracticality of on-line operation monitoring for passive devices such as the above-described devices, it may be advantageous to incorporate various redundancy schemes, to minimize the chance of failure due to unforeseen circumstances. Redundant timing and sensing mechanisms, rendered possible by the extreme miniaturization may be integrated within the device. All critical device components may be built in multiple copies on a single chip, providing parallel fluid and measurement paths in case of failure (e.g., due to channel clogging or sensor malfunction). Single chips may be designed to include multiple sensor chambers for sample analysis, as well as multiple acoustic-emission isolation diaphragms and associated cavities, thus providing multiple assays and hence improved measurement statistics once the devices are recovered at the surface. Multiple timing mechanisms having different time constants may be incorporated onto a single device as well, thus providing a measurement time-series to monitor the evolution of a parameter of interest over a device well injection and retrieval cycle. The resulting device architecture can be extremely robust and should be capable of providing a reliable measurement even in the most adverse environmental conditions.

Harsh Environment Compatibility

Completely passive systems represent an advantageous approach to sensing in the very harsh environments specific to the oilfield (e.g., high temperature and pressure (HPHT), corrosive fluids, severely constrained geometry). The above-described embodiments allow the deployment of smart passive devices that are capable of performing a number of specific, well-defined functions in, without limitation, the subterranean environment surrounding an oil well, without requiring power, monitoring, or telemetry. Such smart passive devices can be deployed downhole by pumping along with frac- or other injected fluids, or they can be integrated within existing oilfield measurement tools such as the MDT tool, the FMT tool or the SFT tool. The smart devices may acquire, react with, and isolate a sample of downhole fluid, and, once retrieved from the reservoir, they can be interrogated by optical, electrical or other means to provide information about the environment they have been exposed to (e.g. chemical or physical properties of the fluids encountered) as well as about the times when the measurements were performed. Additionally, as described above, the device can emit bursts of acoustic signals at pre-defined times which can allow device localization by, without limitation, triangulation using multiple microphones.

All the device functionalities recited above may be implemented in multiple applications, and are not limited in any way to oilfield measurements. Examples of different applications include, but are in now way limited to: submarine deployment of such systems as in a body of water, river, lake, sea, ocean; measurements within water wells and aquifers; waste water storage tanks and reservoirs, and the monitoring thereof; and injection wells for carbone dioxide sequestration.

The above-described embodiments are not constrained to a specific sensing technology—several technologies are compatible with and can be integrated within such a smart passive device, such as, without limitation: purely chemical sensors (e.g. titration reactions), corrosion sensors, MEMS sensors, electrochemical sensors, and functionalized nanoparticles. The purely passive devices may be mission-specific so as to integrate only those functions that are absolutely paramount to performing and later interpreting the specific measurement (or chemical reaction) of interest; all additional functionality will be provided externally after recovery. This purely passive approach therefore minimizes the risk of system failure due to environmental issues.

Ultimate Size Miniaturization

Besides the capability to survive a harsh environment, a fully passive system provides ultimate miniaturization capabilities. Typically, physical transducers occupy only a very small percentage of the total package size in miniaturized sensors (such as those using MEMS technology), the rest being occupied by electronics and connections. A passive approach eliminates the need to operate electronics downhole, and thus can lead to impressive size reduction. The use of small, passive devices, that may be fabricated using, without limitation, MEMS technology, permits deployment within pores and/or fractures of the rock. Such deployment may be performed, for example, as part of a proppant formulation during hydraulic fracturing operations.

In summary, the above-described devices enable a variety of functionalities. These functionalities include, without limitation, the following:

1. mechanical protection and hermetic transport of the device within the external environment (by pumping or injection), or deployment within various measurement tools;

2. sample acquisition, material release and/or chemical reaction in-situ at pre-defined times, using passive microfluidic timing mechanisms;

3. sample isolation from external medium prior to and after acquisition (cross-contamination control);

4. integrated redundancy mechanisms to assure correct device operation even in cases of failure of one of the sample mechanisms;

5. monolythic integration with standard sensor technologies;

6. three-dimensional positioning using coded and/or uncoded acoustic signal emission; and 7. external sensor interrogation capability after retrieval at the surface.

The above-described devices provide robust, highly miniaturized smart passive sample chambers/vessels that can be integrated with several sensor technologies to perform critical in-situ measurements for, without limitation, the oilfield or a living body, or to provide information about the positioning of devices during fluid injection or fracturing operations. One of the main features of the device is its capability to provide a robust timing mechanism to perform, for example, measurements or material release on a pre-defined (or post-inferred) schedule, and/or to emit acoustic signal sequences, which will allow triangulation of the vessel position, thus indicating fluid movement and fracture propagation, within a hydrocarbon reservoir, or other pressurized formation or system. From fracture propagation modeling relative to induced pressures, formation mechanical properties and stress analysis can be performed in-situ. The device may be integrated with standard sensing technologies, allowing a specific measurement or set of measurements to be performed on an isolated fluid sample. The device may also be utilized as part of a proppant formulation during hydraulic fracturing jobs, whereas the passive devices are mixed with slurries and sand grains and are injected alongside into a formation. The device may be used to as a vehicle for time-release of particles, chemical products, or pharmaceutical products.

These combined capabilities result in very versatile a device capable of being implemented within a tool or injected in a formation or living body, to provide measurements on samples acquired and/or to release particles, at different locations in, without limitation, an oil reservoir or body and at multiple times, and to communicate its position via acoustic emission.

The embodiments of the invention described above are intended to be merely exemplary; numerous variations and modifications will be apparent to those skilled in the art. All such variations and modifications are intended to be within the scope of the present invention. These and other obvious modifications are intended to be covered by the claims that follow.

What is claimed is:

1. A device comprising:
an isolated cavity that is initially inaccessible to an exterior environment;
an electrically passive timing mechanism including:
 a timing diaphragm;
 a timing cavity; and
 a microfluidic channel of predefined geometry filled with a timing fluid having known timing fluid properties, such that upon applying pressure to the timing fluid, said timing fluid advances within the microfluidic channel at a speed dictated by the predefined channel geometry and known timing fluid properties; and
a mechanical structure separating the isolated cavity from the exterior environment, wherein upon the timing fluid reaching the timing cavity after a timing interval, the timing fluid applies pressure to the timing diaphragm which ruptures and/or collapses the mechanical structure thus allowing external fluid to enter the isolated cavity, thus bringing the isolated cavity in contact with the exterior environment.

2. The device according to claim 1, further comprising an external device for applying pressure to the timing fluid.

3. The device according to claim 1, wherein the timing fluid is selected from the group of fluids consisting of a Newtonian fluid, a non-Newtonian fluid, a viscoelastic fluid, a yield stress fluid, a shear-thickening fluid, a shear-thinning fluid, and combinations thereof.

4. The device according to claim 1, wherein the mechanical structure includes one of an isolation membrane and an isolation diaphragm.

5. The device according to claim 1, wherein the isolated cavity includes a sampling chamber, the sampling chamber including a check valve that allows flow of fluid into the sampling chamber but prevents flow of fluid out of the sampling chamber.

6. The device according to claim 1, wherein the isolated cavity and/or the mechanical structure are shaped to emit a predetermined acoustic signal upon the mechanical structure collapsing.

7. A system that includes a plurality of devices according to claim 6, wherein each device has an acoustic signature upon rupture and/or collapse of its associated mechanical structure, wherein the acoustic signatures of the devices vary.

8. A system that includes a plurality of devices according to claim 6, wherein the devices are attached to a cable which is further attached to an object selected from the group consisting of a fixed buoy, a surface ship, an underwater vehicle, and combinations thereof.

9. The device according to claim 1, wherein the isolated cavity includes a sensor element for performing a detection and/or a measurement on the fluid.

10. The device according to claim 9, wherein the sensor element includes a material that chemically reacts with the fluid.

11. The device according to claim 9, wherein the sensor element includes an electrode allowing an electrochemical measurement to be performed on the fluid sample.

12. The device according to claim 9, whereas the sensor element includes at least one microelectromechanical MEMS component.

13. The device according to claim 1, wherein there are a plurality of isolated cavities, a plurality of passive timing mechanisms, and a plurality of mechanical structures.

14. The device according to claim 13 where at least one of the passive timing mechanisms has a timing interval different from the other timing mechanisms, such that the mechanical structures associated with the at least one passive timing mechanism ruptures and/or collapses at a different time.

15. The device according to claim 1, wherein the isolation cavity includes a material selected from the group consisting of a micro-particle, a nano-particle, a chemical product, a pharmaceutical product, and combinations thereof, which is released into the environment after the collapse and/or rupture of the mechanical structure separating the isolated cavity from the exterior environment.

16. The device according to claim 15, wherein the device includes a filter and/or a sieve to retain broken mechanical structure parts from entering the isolation cavity and/or the environment surrounding the device.

17. A tool incorporating one or more devices defined by claim 1, the tool having an interior flow-line through which a sample fluid is capable of circulating and in which the one or more devices are positioned, wherein said sample fluid when circulating in the interior flow-line contacts the devices.

18. The tool according to claim 17, further including at least one microphone for receiving acoustic emissions from the one or more devices, the tool further including a processor for performing a timestamping of the received acoustic emissions and/or a determination of device positioning.

19. A method comprising:
deploying a device in an external fluid;
opening an acoustic cavity within the device to the fluid, at a time determined by an electrically passive timing mechanism; and
emitting by the device an acoustic signature when the cavity is opened.

20. The method of claim 19, wherein the passive timing mechanism includes:
a timing diaphragm;
a timing cavity; and
a microfluidic channel of known geometry filled with a timing fluid having known timing fluid properties, such that upon applying pressure to the timing fluid, said timing fluid advances within the microfluidic channel at a speed dictated by the known channel geometry and known timing fluid properties, and upon reaching the timing cavity after a timing interval, the timing fluid applies pressure to the timing diaphragm which opens the acoustic cavity within the device to the external fluid.

21. The method according to claim 19, further comprising detecting the acoustic signature using, at least in part, one or more microphones.

22. The method according to claim 21, further comprising extracting a position of the device from the detected acoustic signature based, at least in part, on a methodology selected from the group consisting of triangulation, compressional signal processing, shear signal processing, and combinations thereof.

23. The method according to claim 19, wherein deploying includes deploying the device within fluid in a structure selected from the group consisting of a geological formation, a formation fracture, a pipe, a well, an engine, a hydrocarbon reservoir, an aquifer, a body of water, an oil field tool, a waste disposal reservoir, a proppant formulation, a living body, and combinations thereof.

24. The method according to claim 19, wherein deploying includes using the device in a hydraulic fracturing operation.

25. The method according to claim 19, further including releasing a material selected from the group consisting of a micro-particle, a nano-particle, a chemical product, a pharmaceutical product, and combinations thereof, stored within the device into the external fluid upon collapse of the acoustic cavity, and/or storing a sample of the external fluid within the device upon collapse of the acoustic cavity.

26. A method comprising:
deploying a device in an external fluid;
opening a cavity within the device to the external fluid, at a time determined by an electrically passive timing mechanism, the passive timing mechanism including:
a timing diaphragm;
a timing cavity; and
a microfluidic channel of known geometry filled with a timing fluid having known timing fluid properties, such that upon applying pressure to the timing fluid, said timing fluid advances within the microfluidic channel at a speed dictated by the known channel geometry and known timing fluid properties, and upon reaching the timing cavity after a timing interval, the timing fluid applies pressure to the timing diaphragm which opens the cavity within the device to the external fluid; and
upon the cavity opening, releasing a material selected from the group consisting of a micro-particle, a nano-particle, a chemical product, a pharmaceutical product, and combinations thereof, from the cavity into the external fluid.

27. The method according to claim 26, wherein deploying includes deploying the device within fluid in a structure selected from the group consisting of a geological formation, a formation fracture, a pipe, a well, an engine, a hydrocarbon reservoir, an aquifer, a body of water, an oil field tool, a waste disposal reservoir, a proppant formulation, a living body, and combinations thereof.

28. A method comprising:
deploying a device in an external fluid;
opening a cavity within the device to the fluid at a time determined by an electrically passive timing mechanism; and
storing a sample of the external fluid within the cavity.

29. The method of claim 28, wherein the passive timing mechanism includes:
a timing diaphragm;
a timing cavity; and
a microfluidic channel of known geometry filled with a timing fluid having known timing fluid properties, such that upon applying pressure to the timing fluid, said timing fluid advances within the microfluidic channel at a speed dictated by the known channel geometry and known timing fluid properties, and upon reaching the timing cavity after a timing interval, the timing fluid applies pressure to the timing diaphragm which opens the cavity within the device to the external fluid.

30. The method according to claim 28, wherein deploying includes pumping the device into a geological formation and/or a formation fracture.

31. The method according to claim 28, wherein deploying includes using the device in a hydraulic fracturing operation.

32. The method according to claim 28, wherein deploying includes deploying the device within fluid in a structure selected from the group consisting of a geological formation, a formation fracture, a pipe, fluid, a well, an engine, a hydrocarbon reservoir, an aquifer, a body of water, an oil field tool, a waste disposal reservoir, a proppant formulation, a living body, and combinations thereof.

33. The method according to claim 28, further comprising emitting by the device an acoustic signature when the cavity is opened.

34. The method according to claim 33, further comprising detecting the acoustic signature using, at least in part, one or more microphones.

35. The method according to claim 34, further comprising extracting a position of the device from the detected acoustic signature based on a methodology selected from of triangulation, compressional signal processing, shear signal processing, and combinations thereof.

36. The method according to claim 28, further comprising upon the cavity opening, releasing a material selected from the group consisting of a micro-particle, a nano-particle, a chemical product, a pharmaceutical product, and combinations thereof, from the cavity into the external fluid.

37. A device comprising:
an isolated cavity that is initially inaccessible to an exterior environment, the isolated cavity including a sampling chamber, the sampling chamber including a check valve that allows flow of fluid into the sampling chamber but prevents flow of fluid out of the sampling chamber;
an electrically passive timing mechanism; and
a mechanical structure separating the isolated cavity from the exterior environment, such that at the end of a timing interval the timing mechanism acts on the mechanical structure to rupture and/or collapse the mechanical structure, thus bringing the isolated cavity in contact with the exterior environment.

38. The device according to claim 37, wherein the isolated cavity includes a sensor element for performing a detection and/or a measurement on the fluid.

39. The device according to claim 38, wherein the sensor element includes a material that chemically reacts with the fluid.

40. The device according to claim 38, wherein the sensor element includes an electrode allowing an electrochemical measurement to be performed on the fluid sample.

41. The device according to claim 38, whereas the sensor element includes at least one microelectromechanical MEMS component.

42. The device according to claim 37, wherein there are a plurality of isolated cavities, a plurality of passive timing mechanisms, and a plurality of mechanical structures.

43. The device according to claim 42, wherein at least one of passive timing mechanisms has a timing interval different from the other timing mechanisms, such that the mechanical structures associated with the at least one passive timing mechanism ruptures and/or collapses at a different time.

44. A tool incorporating one or more devices defined by claim 37, the tool having an interior flow-line through which a sample fluid is capable of circulating and in which the one or more devices are positioned, wherein said sample fluid when circulating in the interior flow-line contacts the devices.

45. The tool according to claim 44, further including at least one microphone for receiving acoustic emissions from the one or more devices, the tool further including a processor for performing a timestamping of the received acoustic emissions and/or a determination of device positioning.

46. A device comprising:
an isolated cavity that is initially inaccessible to an exterior environment;
an electrically passive timing mechanism; and
a mechanical structure separating the isolated cavity from the exterior environment, such that at the end of a timing interval the timing mechanism acts on the mechanical structure to rupture and/or collapse the mechanical structure, thus bringing the isolated cavity in contact with the exterior environment, wherein the isolated cavity and/or the mechanical structure are shaped to emit a predetermined acoustic signal upon the mechanical structure rupturing and/or collapsing.

47. A tool incorporating one or more devices defined by claim 46, the tool having an interior flow-line through which a sample fluid is capable of circulating and in which the one or more devices are positioned, wherein said sample fluid when circulating in the interior flow-line contacts the devices.

48. The tool according to claim 47, further including at least one microphone for receiving acoustic emissions from the one or more devices, the tool further including a processor for performing a timestamping of the received acoustic emissions and/or a determination of device positioning.

49. A system that includes a plurality of devices according to claim 46, wherein each device has an acoustic signature upon rupture and/or collapse of its associated mechanical structure, wherein the acoustic signatures of the devices vary.

* * * * *